United States Patent
Feskov et al.

(10) Patent No.: US 11,091,737 B2
(45) Date of Patent: Aug. 17, 2021

(54) AUTOLOGOUS SOMATIC CELL THERAPY, METHOD OF CONTROLLABLE PREPARATION OF THERAPEUTIC COMPOSITION AND PROCEDURE OF ADAPTIVE TREATMENT OF IVF PATIENT

(71) Applicant: Progena Inc., Bryn Mawr, PA (US)

(72) Inventors: Alexander Feskov, Kharkov (UA); Ievgeniia Zhylkova, Kharkov (UA); Stanislav Zhilkov, Philadelphia, PA (US); Irina Feskova, Kharkov (UA); Vladislav Feskov, Kharkov (UA)

(73) Assignee: Progena Inc., Bryn Mawr, PA (US)

( * ) Notice: Subject to any disclaimer, the term of this patent is extended or adjusted under 35 U.S.C. 154(b) by 0 days.

(21) Appl. No.: 15/688,385

(22) Filed: Aug. 28, 2017

(65) Prior Publication Data

US 2018/0057792 A1    Mar. 1, 2018

Related U.S. Application Data

(60) Provisional application No. 62/494,980, filed on Aug. 29, 2016, provisional application No. 62/494,984, filed on Aug. 29, 2016.

(51) Int. Cl.
| | |
|---|---|
| *C12N 5/0783* | (2010.01) |
| *C12N 5/078* | (2010.01) |
| *A61K 35/14* | (2015.01) |
| *A61K 35/12* | (2015.01) |
| *A61K 38/24* | (2006.01) |

(52) U.S. Cl.
CPC ............ *C12N 5/0636* (2013.01); *A61K 35/14* (2013.01); *A61K 38/24* (2013.01); *C12N 5/0634* (2013.01); *A61K 2035/124* (2013.01); *C12N 2502/11* (2013.01); *G01N 2333/59* (2013.01)

(58) Field of Classification Search
None
See application file for complete search history.

(56) References Cited

U.S. PATENT DOCUMENTS

| 2004/0105858 A1 | 6/2004 | Kim et al. |
| 2013/0172666 A1 | 7/2013 | Feskov et al. |

FOREIGN PATENT DOCUMENTS

WO   WO 2003/022302   3/2003

OTHER PUBLICATIONS

Corkum et al., BMC Immunology, 2015; 16:48 (Year: 2015).*
Head et al., Fertility and Sterility, 2008; 90, Supplement, S232, Abstract p. 373 (Year: 2008).*
Komorowski et al., Immunology Letters, 1997; 59: 29-33 (Year: 1997).*
The abstract by Feskov et al., J Assist Reprod Genet., 2016; 33: 1693-1708, Abstract# 018, p. 1698 (Year: 2016).*
Yu et al., PLOS ONE; doi: 10.1371/journal.pone.0125589, published Jun. 18, 2015; 12 pages total. (Year: 2015).*
Chan et al., Human Reproduction, 2003; 18: 2294-2297 (Year: 2003).*
Zamorina (Biochemistry (Moscow) Supplement Series A: Membrane and Cell Biology, 2014; 8: 37-43 (Year: 2014).*
Mallone et al., Clinical and Experimental Immunology, 2010; 163: 33-49 (Year: 2010).*
Kosaka et al., The Journal of Clinical Endocrinology & Metabolism 87(11):5199-5208 (Year: 2002).*
Yoshioka et al. "Intrauterine administration of autologous peripheral blood mononuclear cells promotes implantation rates in patients with repeated failure of IVF-embryo transfer". Oct. 4, 2006, Human Reproduction vol. 21, No. 12 pp. 3290-3294.
Noorhasan et al. "Serum hCG Levels following the Ovulatory Injection: Associations with Patient\Weight and Implantation Time", Oct. 8. 2015, Hindawi Publishing Corporation Obstetrics and Gynecology International, vol. 2015, pp. 1-6.
Kosaka et al. "Human Chorionic Gonadotropin (HCG) Activates Monocytes to Produce Interleukin-8 via a Different Pathway from Luteinizing Hormone/HCG Receptor System," Nov. 2002, J Clin Endocrinol Metab, 87(11 ):pp. 5199-5208.
Mansour et al. "Intrauterine injection of human chorionic gonadotropin before embryo transfer significantly improves the implantation and pregnancy rates in in vitro fertilization/intracytoplasmic sperm injection: a prospective randomized study," Dec. 6, 2011, Fertility and Sterility, vol. 96, No. 6,pp. 1-6.
Madkour et al. "Intrauterine insemination of cultured peripheral blood mononuclear cells prior to embryo transfer improves clinical outcome for patients with repeated implantation failures," Nov. 6, 2014, Zygote, pp. 1-12.
International Search Report and Written Opinion dated Nov. 13, 2017 issued in corresponding application No. PCT/US17/48889.
International Preliminary Report on Patentability dated Mar. 5, 2019 issued in corresponding PCT application PCT/US2017/048889.
Alexander et al, "HCG Secretion by Peripheral Mononuclear Cells During Pregnancy", *Domestic Animal Endocrinology*, 1998, vol. 15, No. 5, pp. 377-387.

(Continued)

*Primary Examiner* — Christina M Borgeest
(74) *Attorney, Agent, or Firm* — Oblon, McClelland, Maier & Neustadt, L.L.P.

(57) ABSTRACT

A blood product containing peripheral blood mononuclear cells (PBMCs) in an amount of at least 4 million cells per milliliter and human chorionic gonadotropin (HCG in an amount of at least 150 international units (IU) per milliliter. A method of preparing the blood product, including applying HCG to a female patient, then obtaining PBMCs from the female patient, then adding HCG to the obtained PBMCs. A method of culturing PBMCs, including applying HCG to a female patient, then culturing PBMCs obtained from the female patient at a time after the HCG was applied to the patient. A method of in vitro fertilization, including applying HCG to a female patient, culturing PBMCs obtained from the patient after the HCG was applied to the patient, introducing the cultured PBMCs into the uterus of the patient, and transferring at least one embryo into the uterus of the patient.

5 Claims, No Drawings

(56) References Cited

OTHER PUBLICATIONS

Y. M. Zhang et al, "Macrophages in Human Reproductive Tissues Contain Luteinizing Hormone/Chorionic Gonadotropin Receptors", *Am J Reprod Immunology*, 2003, vol. 49, Issue 2, p. 93-100 Abstract only 1 page https://onlinelibrary.wiley.com/doi/abs/10.1034/j.1600-0897.2003.00013.x.

Zygmunt et al, "HCG increases trophoblast migration in vitro via the insulin-like growth factor-11/mannose-6 phosphate receptor", *Molecular Human Reproduction*, 2005, vol. 11, No. 4, pp. 261-267.

Zhang et al, Negative regulatory role of mannose receptors on human alveolar macrophage proinflammatory cytokine release in vitro', *Journal of Leukocyte Biology*, 2005, vol. 78, 665-674.

Schumacher et al, "Human Chorionic Gonadotropin Attracts Regulatory T Cells into the Fetal-Maternal interface during Early Human Pregnancy", "*Journal of Immunology*", 2009, vol. 182, pp. 5488-5497.

Kane et al, "Proliferation of uterine natural killer cells is induced by hCG and mediated via the mannose receptor", *Endocrinology*, 2009, vol. 150, No. 6, (13 pages).

Evans et al, "Too much of a good thing? Experimental evidence suggests prolonged exposure to hCG is detrimental to endometrial receptivity", *Human Reproduction*, 2013, vol. 28, No. 6, pp. 1610-1619.

Thiruchelvam et al, "The importance of the macrophage within the human endometrium", *Journal of Leukocyte Biology*, 2013, vol. 93, pp. 217-225.

Liang et al, "The high concentration of progesterone is harmful for endometrial receptivity and decidualization" www.nature.scientificreports published online Jan. 15, 2018 . . . (12 pages).

Supplemental Search Report dated Jul. 16, 2020, in European patent application No. EP 17 8473006.2 ( 10 pages).

Examination report No. 2, for standard patent application dated Sep. 1, 2020, in Australian patent application No. 2018203649 (3 pages).

Fujiwara et al, "Do circulating blood cells contribute to maternal tissue remodeling and embryo-maternal cross-talk around the implantation period?", *Molecular Human Reproduction*, 2009, vol. 15, No. 6, pp. 335-343.

Thompson et al, "Gonadotrotrophin requirements of the developing follicle", *Fertility and Sterility*, 1995, vol. 63, No. 2, pp. 273-276.

Abstracts of the 35th Annual Meeting of the ESHRE, Vienna, Austria Jun. 24 to 26, 2019, i337-i338, (5 pages).

Anette Kullmann, et al., *Avoid Artifacts: Isolate Pure and Functional Monocytes from PBMC, Buffy Coat or Whole Blood using Dynabeads® FlowComp™*, http://tools.thermofisher.com/content/sfs/posters/Human-CD-14.pdf, created Jan. 15, 2010, accessed Sep. 16, 2020 (1 page).

\* cited by examiner

//AUTOLOGOUS SOMATIC CELL THERAPY, METHOD OF CONTROLLABLE PREPARATION OF THERAPEUTIC COMPOSITION AND PROCEDURE OF ADAPTIVE TREATMENT OF IVF PATIENT

CROSS REFERENCE TO RELATED APPLICATIONS

This application claims priority to U.S. provisional application Nos. 62/494,980 and 62/494,984, filed on Aug. 29, 2016, the entire contents of each of which are hereby incorporated by reference.

BACKGROUND OF THE INVENTION

Field of the Invention

The present invention relates to in vitro fertilization (IVF).

Discussion of the Background

Assisted reproduction technology (ART), including IVF, has demonstrated significant progress in infertility treatment Overall, ART contributed 1.4% of births in the US in 2009, ranging from 0.2% in Puerto Rico to 4.3% in Massachusetts [Saswati Sunderam et al., 2012]. In Europe, the share of ART infants per national births was from 0.8% in Montenegro to 4.1% in Denmark in 2006 [J. de Mouzon et al., 2010].

However, a significant share of embryos created and transferred by IVF methods still fail to be implanted, and this share is estimated to be in the range from 60% to more than 80%. [See Alex Simon and Neri Laufer 2012; see also J. de Mouzon et al. 2010 for Europe and Arefi et al. 2008 for Middle East].

Repeated implantation failure (RIF) typically is defined as failure of implantation in at least three consecutive IVF attempts, in which 1 to 2 embryos of high grade quality are transferred in each cycle. Both fresh- and cryo-IVF are included in this definition. "Fresh-IVF" means that the implantation is performed without freezing or thawing of the oocyte or embryo. "Cryo-IVF" means that freezing and thawing of the oocyte or embryo is performed prior to implantation.

Some experts estimate that one third of early pregnancy failures, spontaneous abortions and biochemical pregnancies (not leading to inception), are due to chromosomal abnormalities, while the remaining two thirds are due to inappropriate implantation [Cole 2012]. According to other opinions, the share of implantation failures that might be related to autoimmune causes is estimated to be in the range from 10 to 40% [Feskov et al. 2013].

The success of implantation depends on a receptive endometrium, a normal blastocyst and synchronized cross-talk at the maternal-fetal interface. The progression of pregnancy then requires immunological tolerance, which allows conceptus survival. The mechanisms underlying human implantation, and particularly immune tolerance of pregnancy, remain to be defined in detail. A role of the prime hormonal mediator, by which the embryo announces its presence to the maternal organism, might be assigned to human chorionic gonadotropin (HCG), since production of this hormone by the embryo is observed before any others and even before implantation. Among the wide range of mediators present at the implantation site, a pivotal role is becoming evident for HCG: as a specific blastocyst signal, HCG is involved in orchestrating the implantation cascade, while, at the same time, HCG also is produced by the endometrium. HCG is involved in several actions that promote immunological tolerance, angiogenesis and tissue growth, and thus has physiologically important implications for successful pregnancy [See Tsampalas M et al. 2010; Cole 2009, 10, 11, 12; see also Alex Simon and Neri Laufer 2012].

Dual regulation of human embryo implantation is provided by hormones and circulating immune cells. Signals from a developing embryo in the genital tract are transmitted to the ovary not only by the endocrine system, but also by the immune system, in other words, via not only soluble factors (such as HCG), but also via circulating cells, such as peripheral blood mononuclear cells (PBMC) and peripheral blood cells without nuclei (platelets). The maternal immune system recognizes the presence of the developing and implanting embryo in the Fallopian tube and the uterus by embryo- and species-specific signals such as degraded products of zona pellucida glycoprotein and/or HCG. Then, effector immune cells move to the ovary and the endometrium via blood circulation to regulate the function of corpus luteum and induce the endometrial differentiation. The local immune cells at the implantation site also contribute to induction of embryo invasion, secreting chemoattractants by HCG stimulation. The circulating immune cells transmit information about the presence of the developing embryo to various organs throughout the whole body and induce adequate functional change or differentiation in these organs to facilitate embryo implantation [Yoshioka, Fujiwara et al. 2006; especially Fujiwara 2009 and 2012].

HCG

HCG has been recognized as having fundamental importance in controlling the preconditions, inception, establishment, development, maintenance and ultimate success of human pregnancy. It is difficult to overestimate the role of HCG in immune and endocrine system of humans and even in the evolution of humans. [Cole 2009, 2010, 2011, 2012 and 2013; Tsampalas M et al. 2010; Fujiwara 2009 and 2012].

Known biological functions of HCG during pregnancy are as follows [Cole 2012]:
1) Promotion of corpus luteal progesterone production;
2) Angiogenesis of uterine vasculature (maternal tissue growth);
3) Cytotrophoblast differentiation;
4) Immuno-suppression and blockage of phagocytosis of invading trophoblast cells;
5) Growth of uterus in line with fetal growth;
6) Quiescence of uterine muscle contraction;
7) Promotion of growth of fetal organs;
8) Umbilical cord growth and development;
9) Blastocyst signaling to uterine decidua prior to invasion regarding pending implantation;
10) HCG in sperm and receptors found in fallopian tubes suggesting pre-pregnancy communication;
11) HCG receptors in hippocampus and brain stem, may cause nausea and vomiting in pregnancy;
12) Stimulation of implantation by invasion of cytotrophoblast cells as occurs at inception of pregnancy;
13) Stimulation of growth of placenta by promoting growth of cytotrophoblast cells; and
14) Driving the hemochorial placentation.

The amount of HCG in the maternal body grows exponentially from 1 IU per liter to the order of hundreds of thousands of IU per liter during the first five weeks of pregnancy [Grenache 2009]. In serum, in the 4th week of gestation (weeks following start of menstrual period), individual total HCG values vary by 824-fold, between 0.21 and 173 ng/ml amongst different women with singleton term outcome pregnancies. In the 5th week of gestation, total HCG values vary by 704 fold, between 1.86 and 1308 ng/ml amongst different women with singleton term outcome pregnancies. Individual HCG daily amplification rate is a major cause of variation in early days/weeks of gestation. [Cole 2010].

There are over a dozen different forms and isoforms of HCG, among which "hCG" is the endocrine or hormone made by placental syncytiotrophoblast cells, while "Hyperglycosylated hCG" is the autocrine made by placental cytotrophoblast cells during pregnancy [Cole 2013]. In the human body, the sulfated form of HCG is secreted by the pituitary gland. Other human tissues and cells also are capable of expression or production of some forms of HCG. Epithelial HCG is expressed and produced in human secretory endometrium [Zimmermann et al. 2009]; the proper functioning of this process is very important for a healthy pregnancy.

Secretion of HCG by PBMCs of pregnant woman was specifically studied to find out how they contribute to implantation and early development of pregnancy. The earliest HCG secretion was observed 5 to 9 days after the embryo transfer in IVF patients. Surprisingly, the NK cells that express the Fc(RIII) receptor (CD16+) and the adhesion molecule NCAM (CD56+) are the most potent cells in HCG secretion and not as expected the T lymphocytes. Likewise, monocytes (CD14+) are effective in HCG secretion and less T helper cells (CD4+). [Alexander et al. 1998].

Different tissues/cells have suitable receptive sub-structures for interacting with HCG. The HCG receptor, which is shared with luteinizing hormone (LH), was subsequently demonstrated on T and B lymphocytes [Amolak S Bansal et al., 2012]. LH/HCG receptors are widely distributed not only in gonadal, but also in non-gonadal tissues including the female tract (oviduct, uterus, myometrium, endometrium, uterine vessel), placenta, mammary gland, brain, skin, epididymis, urinary bladder and umbilical cord. Recently, the association of neuronal LH/HCG receptor expression with sensory, memory, reproductive behavior and autonomic structures also has been identified [Ziecik A. J. et al. 2007].

The impact of HCG on uNK (uterine natural killer) cells is mediated via the mannose receptor (CD206) [Nicole Kane et al. 2009].

Human monocytes respond to HCG and secrete interleukin IL-S through a pathway different from the LH/HCG receptor system, suggesting that this glycoprotein hormone can react with not only endocrine cells but also immune cells early in pregnancy, probably via primitive systems such as C-type lectins. [KENZO KOSAKA, HIROSHI FLUJIWARA et al., 2002]. HCG adsorbs to surfaces, including membranes of tissues that lack specific HCG receptors [Cruz et al., 1987].

Infusion of HCG into the oviducts of baboons to mimic embryo transit induces a myriad of morphological, biochemical, and molecular changes in the endometrium. There exists a certain pathway, which is activated by HCG, and this pathway regulates prostaglandin production by the endometrial epithelium and serves as an early trigger to prepare the endometrium for implantation [Prajna Banerjee et al. & Fazlcabas 2009].

HCG significantly increases the production of six cytokine factors that are secreted by glandular epithelium into the uterine cavity. Among the increased factors are those with known roles in receptivity and trophoblast function (interleukin-11), blastocyst migration and adhesion (CXCL10), blastocyst development (granulocyte macrophage colony-stimulating factor), fibroblast growth factor 2 (FGF2) and several other cytokines produced by human endometrial epithelial cells. This provides a mechanism for enhancing endometrial receptivity under the influence of HCG [Paiva et al. 2011].

HCG and growth factors at the embryonic-endometrial interface control leukemia inhibitory factor (LIF) and interleukin 6 (IL-6) secretion by human endometrial epithelium. Through HCG, the blastocyst may be involved in the control of its implantation (via an increase of preimplantation role of LIF) and tolerance (via an inhibition of pro-inflammatory IL-6). [Perrier d'Hauterive 2004].

HCG is secreted from the developing and implanting human embryo. It is generally thought that HCG is an embryo-specific signal for maternal recognition by the immune system [Fujiwara 2012].

Effects of HCG and beta-HCG on secretion of cytokines (as IL-2 and sIL-2R) from human PBMC have been found [Komorowski et al. 1997]. This was early evidence that an immune-endocrine network involving HCG and peripheral blood immune cells exists and plays an important role in early pregnancy. The modulating impact of HCG on the maturation and function of such cells has been demonstrated rather comprehensively.

Peripheral blood monocytes (PBMC or PBMCs herein) are able to respond to HCG at high concentrations by enhancing their production of IL-8. [KENZO KOSAKA, HIROSHI FUJIWARA et al., 2002]. Immature dendritic cells (DC), which were generated from blood-derived monocytes and differentiated in the presence of HCG, had significantly reduced T-cell stimulatory capacity after HCG exposure, and this may help in preventing an allogenic T-cell response against the embryo [Sabine E. Segerer et al. 2009].

The application of HCG for IVF patient increases maternal PBMC. HCG was shown to increase anti-inflammatory IL-27 expression, and reduce inflammatory IL-17 expression, in women who received HCG as preconditioning prior to IVF. In addition, increased IL-10 levels and elevated numbers of Tregs in peripheral blood were found in women after HCG application. The Th1/Th2 balance after HCG treatment was improved toward better immune tolerance. Rejection of allogeneic skin grafts was delayed in female mice receiving HCG. These findings suggest that HCG may be useful for the induction of immune tolerance, not only in pregnancy inception, but also in solid organ transplantation. [Michael Koldehoff et al. 2011].

Some postulate that HCG has a profound ability to alter maternal immune function with a view to promoting tolerance to the haploidentical fetus. [Amolak S Bansal et al. 2012]. This involves increasing Treg recruitment and activity at the feto-maternal interface and a downregulation of Th1 and Th17 activity. HCG also alters dendritic cell activity via an up-regulation of function of indoleamine dioxygenase (IDO) that favorably skews T-cell tolerance. The importance of HCG in encouraging angiogenesis may be relevant to preeclampsia via impaired placentation that reduces fetal nutrition. There is a similarity between the HCG/LH receptor and TSH receptor, which raises the possibility of autoantibodies to the HCG/LH receptor and HCG itself. Autoimmunity to HCG and its receptor may be the cause of recurrent failed IVF and recurrent early miscarriage in some women.

Although not all mechanisms of HCG-related influences are understood, recently there have been several attempts to apply HCG in treatment of patients having either a history of RIF or a risk of implantation failure. With the assumption of immune/endocrine cause of IVF failure, it was expected that the administration of HCG would contribute to balancing of embryo-mother interaction and promote inception of pregnancy that could not be achieved otherwise.

Direct injection of HCG into the uterus 5 to 10 minutes prior to embryo transfer has been evaluated in a specific clinical trial [Ragaa Mansour et al. 2011]. The HCG injection in an amount of 100 or 200 IU did not show a difference compared to a control group, while a dose of 500 IU led to an increase of implantation rate.

Indirectly, it was proposed to use HCG for activation of cultured PBMCs, which were further injected into the uterus 24 hours prior to embryo transfer [Yoshioka, Fujiwara et al, 2006]. The dose of HCG sufficient to produce 5 IU/ml concentration in a culture media was applied. Increase of implantation rate was demonstrated compared to a control group.

Cole proposed a use of H-hCG to increase the likelihood of an implantation. It was hypothesized a possible usefulness of administration of a composition containing H-hCG to a patient during a period of time from a few days before implantation to a few days after it; while the administration was supposed to maintain the serum H-hCG at a level ranging from 0.1 to 10 nanograms/ml of serum during that period of time. For maintaining an effective concentration of H-hCG through an intravenous route of administration, an intravenous dose within the range 1 to 50 microgram at least once and up to four times a day was proposed. It was also mentioned that a composition may be prepared in a formulation suitable for vaginal administration. In support of the proposed, this patent application exploited observations of nearly one hundred cases of natural cycles when pregnancy was achieved or failed and the certain correlation of the serum H-hCG with natural cycle outcome was shown. [L. Cole, US Pat Application Number 20070020274, Jan. 25, 2007]

Bae et al. have shown that the triggering with high dose hCG can bring favorable outcomes in IVF cycles with GnRH antagonist protocol, allowing to increase the invasive potential of trophoblast-derived cells. They pointed out that the plasma metabolic clearance rate of hCG is slower than that of LH, and between urinary and recombinant hCG, u-hCG has slightly longer half-life than r-hCG: Calculated initial half-life of r-hLH, r-hCG and u-hCG was determined as 0.8±0.2, 4.7±0.8 and 5.5±1.3 hrs. Rate of clinical pregnancy was significantly higher in double dose hCG triggering groups (500 micro-grams of r-HCG or 10,000 IU of u-HCG) than single dose hCG triggering group (5,000 IU of u-HCG) in fresh IVF cycles with the GnRH antagonist protocol that assumed administration of HCG 36 hours in advance of measurement of its serum concentration [J. Bae et al. Does high dose hCG triggering bring favorable outcomes in IVF cycles with GnRH antagonist protocol? ESHRE 2014 Poster www.posters2view.eueshre2014/data/380.pdf].

PBMC

PBMCs are multipotent cells. Monocyte-derived adult stem cells, isolated from peripheral blood (especially, CD14+ monocytes), have been identified. Under conditions of proper culturing, the multipotent cells can differentiate into any kind of human tissue, including endothelium [EP1581637; U.S. Pat. Nos. 7,795,018; 8,216,838].

PBMCs contribute to maternal tissue remodeling and embryo-maternal cross-talk around the implantation period [Fujiwara 2009 and 2012]. Specifically, PBMCs of early-pregnant women can promote the invasion of BeWo cells (placenta development) and can stimulate progesterone production, suggesting that circulating blood immune cells in early pregnancy enhance the function of corpus luteum. PBMC are also found to be capable of promoting the receptivity of human endometrial cell.

The injection of autologous PBMC (without mentioning any prior activation by HCG) was shown to be effective for treatment of patients with repeated implantation failures in IVF therapy [Okitsu et al. & Fujiwara 2011].

It was shown that if PBMC from non-pregnant women are incubated with HCG, then these HCG-treated PBMC promote propagation of BeWo cells more effectively than non-treated PBMC. This led to the important conclusion that HCG could change PBMC functions to facilitate embryo implantation. Consequently, a fresh-IVF procedure with pretreatment by the PBMC has been explored, with the PBMC cultured in HCG-enriched media prior to administration. Certain success in preventing implantation failure has been demonstrated with this approach [Fujiwara 2006 and 2007]. Several possible mechanisms relevant to the above-mentioned procedure have been proposed as follows:

1) PBMC may induce endometrial differentiation that facilitates embryo attachment;

2) Although PBMC are autologous cells from the patient, the induction of PBMC by themselves is expected to evoke favorable inflammatory reactions in the uterine cavity in vivo;

3) PBMC can secrete proteases that may effectively change the function or structure of surface molecules expressed on endometrial luminal epithelial cells; and 4) PBMC can move from the uterine cavity toward the endometrial stromal tissue, creating a leading pathway for subsequent embryo attachment and invasion [Fujiwara 2009 and 2012].

In humans, monocytes and NK cells are the first immune cells (of all PBMCs) that come in contact with the embryo, and this can contribute to the development of embryo-maternal dialogue to induce immunotolerance. The woman's immune reactive cells by themselves support this tolerance development, when they produce HCG [Alexander et al. 1998]; production of HCG by PBMCs was shown as early as at 5th day of pregnancy of IVF patient.

BRIEF SUMMARY OF THE INVENTION

In view of difficulties in implantation during IVF described above, it is an object of the present invention to combine HCG and PBMC to achieve successful implantation. The present inventors have found a new approach to solve problems of known techniques and methodologies. An object of the present invention has been achieved by the inventors' research that (i) HCG can induce its own production by the cultured PBMC of non-pregnant women, and (ii) a significant increase in a successful implantation rate can be obtained if embryo transfer is performed when the in-vitro culturing process achieves certain indicative parameters exceeding their cutoff values, and is synchronized with in vivo processes that also involve HCG.

An object of the present invention is to provide a blood product, comprising:

peripheral blood mononuclear cells (PBMCs) in an amount of at least 15 million cells per milliliter, and human chorionic gonadotropin (HCG) in an amount of at least 500 international units (IU) per milliliter.

In another embodiment, at least a first portion of the PBMCs is derived from blood of a female patient, wherein the blood was obtained from the female patient after HCG had been applied to the female patient.

In another embodiment the first portion of the PBMCs has been cultured in vitro in the presence of HCG, after the blood from which the first portion of the PBMCs is derived was obtained from the female patient.

In yet another embodiment, a second portion of the PBMCs is derived from blood of the female patient, wherein the blood was obtained from the female patient at a later time than was the blood from which the first portion of the PBMCs was derived.

In a different embodiment, the blood from which the second portion of PBMCs is derived is obtained from the female patient at a time of 20 to 80 hours, preferably of 45+/−5 hours after the blood from which the first portion of PBMCs is derived was obtained from the female patient.

In one embodiment of the blood product, the HCG was applied to the female patient in an amount sufficient to maintain a serum HCG level in a range of 150 to 350 IU/ml, preferably of 250+/−50 IU/ml in vivo at the time the blood was obtained from the female patient.

In another embodiment of the blood product, the PBMCs comprise $CD14^+$ monocytes, preferably comprising $CD14^+$ in a larger proportion, compared to this monocyte's presence in a non-manipulated blood of the patient.

Another object of the present invention is to provide a method of preparing the above blood product, comprising
  applying HCG to a female patient at a time T0;
  obtaining PBMCs from the female patient at a time T1, where T1>T0; and
  adding HCG to the obtained PBMCs.

In one embodiment, T1−T0 ranges from 30 to 40 hours. In a preferred embodiment, T1−T0 is about 36 hours.

Another object of the present invention is to provide a method of preparing the above blood product, comprising
  obtaining the second portion of the PBMCs; and
  adding the second portion of the PBMCs to the first portion of the PBMCs.

Another object of the invention is to provide a method of culturing peripheral blood mononuclear cells (PBMCs), comprising:
  applying human chorionic gonadotropin (HCG) to a female patient at a time T0; and
  culturing peripheral blood mononuclear cells (PBMCs), obtained from the female patient at a time T1, where T1>T0, in a culture medium until a time T2, wherein T2>T1.

In one embodiment, T1−T0 ranges from 30 to 40 hours. In a preferred embodiment, T1−T0 is about 36 hours.

In one embodiment, T2−T1 ranges from 20 to 80 hours. In another embodiment, T2−T1 is about 45+/−5 hours.

One embodiment includes measuring a concentration of HCG in the PBMC culture at least once during the period from T1 to T2.

Another embodiment includes applying HCG to the female patient by injecting HCG intramuscularly.

In one embodiment, the HCG is applied to the female patient in an amount sufficient to maintain a serum HCG level of 250 IU/ml in vivo at the time T1.

Another object of the present invention is directed to a method of in vitro fertilization for a female patient, the method comprising:
  applying human chorionic gonadotropin (HCG) to the female patient at a time T0;
  culturing peripheral blood mononuclear cells (PBMCs), obtained from the female patient at a time T1, wherein T1>T0, in a culture medium;
  introducing the cultured PBMCs into the uterus of the female patient; and
  transferring at least one embryo into the uterus of the female patient.

In one embodiment, T1−T0 ranges from 30 to 40 hours. In a preferred embodiment, T1−T0 is about 36 hours.

In one embodiment, the applying of HCG to the female patient comprises injecting HCG intramuscularly.

In another embodiment, the HCG is applied to the female patient in an amount sufficient to maintain a serum level of 250 IU/ml in vivo at the time T1.

In another embodiment, the female patient suffers from recurrent implantation failure, autoimmune infertility, idiopathic infertility, or is of age >37 years.

DETAILED DESCRIPTION OF THE INVENTION

All publications, patent applications, patents, and other references mentioned herein are incorporated by reference herein in their entirety. Further, the materials, methods, and examples are illustrative only and are not intended to be limiting, unless otherwise specified.

The following detailed description illustrates exemplary embodiments of the present invention. However, the invention is not limited to these exemplary embodiments.

The present inventors have found a correlation between the outcome of IVF (e.g., implantation success rate) and measurable parameters (e.g., HCG concentration in culture media, in vitro process stage duration, moment of time of embryo transfer, etc.). This correlation allows, through real-time changes in the procedure, a reduction in the risk of implantation failure. In some cases, the measured parameters suggest a low probability of successful implantation. In these cases, the thawing of an embryo can be postponed, or embryo transfer even can be avoided. In this way, the embryo can be preserved for a better chance of implantation at a later time. This better chance can be approached if appropriate dynamics are demonstrated by the measurements, and such dynamics can be first achieved in the course of a "training session" (without thawing of the embryo). After such a training session, the appropriate dynamics can be reproduced for actual transfer of the embryo. Important measurements of HCG concentration may be taken at pre-determined moments of time (e.g., T0, T0+24 hours, T0+48 hours) and the changes, if necessary, may be implemented relative to these moments.

In some embodiments, the present invention provides an autologous somatic stem cell therapy for treatment, mitigation or prevention of a medical condition, wherein the therapy is for a female patient undergoing in vitro fertilization (IVF), wherein a medical condition is a risk of implantation failure or of early miscarriage or of spontaneous abortion, wherein the patient's own cell or a set of the patient's cells is engaged in interacting with an implantation agent, wherein engagement of the cell or of the set in the interacting allows to approach a goal of the therapy e.g. to reduce the risk, wherein an implantation agent is human chorionic gonadotropin (HCG), and wherein the therapy accomplishment combines three synchronized processes A, B and C as follows:

A. In-vivo process lasting between moments of time T0 and T2; the process A comprising steps:
  A1 applying a first direct portion of HCG to the patient at moment of time T0,
  A2 allowing said HCG to interact with the cell or the set inside the patient's body until T2, B. In-vitro process lasting between moments of time T1 and T2; the process B comprising steps:

B1 preparing a culture media with HCG at moment of time T1 while T0<T1<T2 (T1~T0+36 hr), B2 taking a sample of the patient's blood, extracting an initial portion of peripheral blood mononuclear cells (PBMC) from the patient's blood and placing the initial portion of PBMC into a culture media at T1, B3 culturing the PBMC in the culture media until moment of time T2, while performing at least one measurement of HCG during period from T1 to T2 and optionally adding HCG to the culture after said measurement or/and optionally applying prolongation of culturing until (T2+ΔT2), to obtain a first blood product, B4 taking another sample of the patient's blood, extracting another portion of PBMC, placing said portion into the culture where initial PBMC has been cultured since T1 (i.e., into the first blood product), measuring a content of HCG in the media after this placing at moment of time T2 or (T2+ΔT2) and optionally adding HCG to the culture after said measurement, B5 producing a composition (i.e., a second blood product) from long-cultured and freshly extracted PBMC at T2 or (T2+ΔT2), C. In-vivo process starting from moment of time T2 after the process A; the process C comprising steps:

C1 intrauterine applying of the composition (B5) to the patient at moment of time T2 or (T2+ΔT2), C2 applying second direct portion of HCG to the patient at moment of time T3 (as T2 plus 24 to 72 hr), C3 transferring an embryo to the patient's uterus cavity assuming that said embryo begins intrauterine producing of HCG at moment of time (T3+ΔT3), C4 optionally applying a 3rd direct portion of HCG to the patient at moment of time T4 (as T3+2 days), C5 optionally applying a 4th direct portion of HCG to the patient at moment of time T5 (as T3+4 days).

The administering of therapy that accomplished through the synchronized processes significantly reduces the risk of implantation failure compare with IVF procedure without such synchronized processes.

In some embodiments, the set of the patient's cells comprises peripheral blood cell without nuclei (platelets), peripheral blood mononuclear cells (PBMCs), other cell or cells, or a combination thereof, and wherein the interacting might be realized in the course of at least one in vivo or in vitro process. In some embodiments, the PBMCs of steps B2 to B5 are $CD14^+$ monocytes.

In some embodiments, one or more of the direct portions of HCG applied in steps A1, C2, C4 and C5 are applied in the form of intramuscular injection of a solution comprising HCG. Each injection may contain the same or different amounts of HCG, for example in a range of 1500 to 15,000 IU per injection, or 5,000 to 10,000 IU per injection.

In some embodiments, the second direct portion of HCG (step C2) might be an intramuscular injection of a solution with HCG, or an intrauterine injection of a slurry with HCG, or any combination of quasi-simultaneously applied intramuscular injection of the solution and intrauterine injection of the slurry. Each injection of slurry may contain the same or different amounts of HCG, for example 100 to 500 IU.

In some embodiments, the cells of a donor are involved in the culturing according to the step B3 and/or B4 or in the producing of the compositions according to the step B5, wherein the donor is immunologically identical to the patient. In some embodiments, one or more substances in addition to HCG may be applied. The substances may be introduced into one or more of the three processes A, B and C, or prior to or in between process steps. Such substances include, for example, CSF (colony stimulating factor), G-CSF (granulocyte-CSF), GM-CSF (granulocyte macrophage-CSF), HLA-G (human leucocyte antigen G), IL (interleukin), and LIF (leukemia inhibitory factor).

In some embodiments, during at least one of the three processes the cell is engaged in interacting with an implantation agent, wherein the interacting might be local or systemic, and wherein the local interacting might be attracting, absorbing, producing, releasing, expressing, transforming of the agent by the cell or transforming of the cell by the agent.

In some embodiments, the systemic interacting might lead to growing of population of cells of a type similar to the cell initially involved into the local interacting, lead to engaging of other cells of different type into their interacting with the agent, or lead to engaging of other cells of different type to be intermediary in the interacting of the agent with the cells of type similar to the initially involved cell.

In some embodiments, the cell comprises a sub-cellular structure suitable for the interacting, while said sub-cell structure might be a receptor specific for, an adhesion molecule specific for, a cellular membrane linkable with the agent, or/and another sub-cellular structure suitable for the interacting.

In some embodiments, the invention includes a method of controllable preparation of a therapeutic composition, such as a blood product, for the above therapy, wherein the method uses a composition comprising PBMC and HCG, wherein the method comprises two or more measurements of concentration of HCG in the patient's blood sample or in the culture media of the process B where the interacting of PBMC and HCG takes place, wherein said measurements are performed at different preliminary-scheduled moments of time, and, wherein, depending on results of said measurements, a decision shall be made as following:

to proceed with predetermined procedure of culturing PBMC in the culture media and perform the embryo transfer, or to apply changes to the procedure of culturing PBMC in the culture media and perform the embryo transfer; or to apply changes to the procedure of culturing PBMC in the culture media but postpone thawing of the embryo; or to reconsider efficacy of the composition-based therapy and postpone its administration.

In some embodiments, a dose of the PBMC+HCG composition, which is to be obtained for intrauterine administration to the patient, is in the range of 0.10 to 0.35 mL of the washed suspended substance of PBMC+HCG having a concentration of PBMC from 4 million to 8 million cells per milliliter and/or a content of HCG from 100 to 500 IU per dose.

In some embodiments, the culture media of the process B comprises an activator for enhancing of the interacting, wherein the activator is a cytokine such as GM-CSF, IL or another cytokine, or a non-cytokine activator such as TKA or another non-cytokine activator, or a combination of one or more cytokine and/or non-cytokine activators.

In some embodiments, the decision is made if all measurements of HCG are in proper ranges, for example if C0 and C48 for total HCG are in proper ranges, or if C0 and C48 for beta-HCG are in proper ranges.

In some embodiments, the decision is selected complementary to a dynamics of expression of HCG in the patient's blood samples or/and in the culture media, and wherein the changes applicable to the procedure of culturing are selected from the following: additional input of HCG into the media, addition of the donor's cells into the media, addition of activator into the media, prolongation of time of culturing, restructuration of ratio of long-cultured cells to freshly extracted cells in course of production of the composition, or any combination thereof, or no changes required.

In some embodiments, the dynamics is preliminary determined in course of a training session, during which the patient's PBMC are cultured, but the frozen embryo is not thawed for transferring.

In some embodiments, the dynamics shall demonstrate an increase of concentration of HCG during interval of culturing and the final concentration of HCG at the end of culturing is to be in a proper range.

In some embodiments, the dynamics shall be such that the absolute increase of concentration of HCG from moment T10 . . . to T10 . . . during an interval of culturing is to be in an acceptable range of increase; it might be a later point T10 . . . minus earlier point T10 . . . equals to 24+/−3 hours, or 48+/−3 hours, or 72+/−3 hours.

In some embodiments, the dynamics are such that the relative increase of concentration of HCG between control points T10 . . . and T10 . . . within an interval of culturing is to be in an acceptable range; it might be a later point T10 . . . minus an earlier point T10 . . . equals to 24+/−3 hours, or 48+/−3 hours, or 72+/−3 hours.

In some embodiments, the HCG might be recombinant HCG, urinary HCG, or an isoform of HCG, such as hyperglycosylated HCG, beta HCG, or any other isoform of HCG, or a functional portion of any isoform of HCG, or any variant of fusion of at least two isoforms of HCG, or any other combination of isoforms of HCG, or total HCG, and wherein the measurements might deal with determining the concentration of at least one isoform from mentioned variety of isoforms of HCG.

In some embodiments, the measurements determine the concentrations of two or more different isoforms of HCG.

In some embodiments, the media's concentration of beta HCG is measured, the results of measurements exceed the indicative parameters both for C0 (at the starting point of culturing) and C48 (48 hours later), and the PBMC culturing and embryo transfer procedure is begun.

In some embodiments, the media's concentration of beta HCG or the media's concentration of total HCG is measured, wherein time T100 is determined as the starting point of culturing, time T101 is determined as 24+/−2 hours from the starting point of culturing, time T102 is determined as 48+/−2 hours from the starting point of culturing, and wherein the acceptable range of absolute increase of respective concentration is known a priori due to statistical analysis of plurality of previous implantation cases.

In some embodiments, the media's concentration of HCG is measured, and the acceptable range of relative increase is known a priori due to statistical analysis of plurality of previous implantation cases.

In some embodiments, the media's concentration of total HCG is measured, the results of measurements exceed the indicative parameters both for C0 (starting point) and C48 (48+/−2 hours after starting point), and the PBMC culturing and embryo transfer procedure is begun.

In some embodiments, the media's concentration of total HCG is measured, the results of measurements are below the indicative parameters C0 and C48, and the PBMC culturing and embryo transfer procedure is postponed, thus saving an embryo.

In some embodiments, the media's concentration of total HCG is measured, the control points T101 and T102 are respectively determined as (24+/−2 hours) and (48+/−2 hours) from starting point of culturing, and the acceptable range of relative increase of the concentration is from 1.05 to 1.35 times.

In some embodiments, the $CD14^+$ monocyte with linked HCG is a major component of the first or second blood product. The linkage may be due to the cellular membrane.

In some embodiments, the cell is engaged in interacting with HCG as follows:
  dendritic cell (DC), while the interacting leads to reduced antigen-presenting function, to reduced DC proliferation and to skewing of T-cell function of escalation Th1 and Th17; or
  endothelial cell, while the interacting leads to stimulation of vascular endothelial growth factor (VEGF), to increased endothelial proliferation, and to reduced leukocyte adhesion; or
  extravillus trophoblast cell (EVT), while the interacting leads to increased invasion of maternal spiral arteries, to apoptosis of activated T cells, and to favorable regulation of FAS/FAS ligand expression; or
  Treg cell, while the interacting leads to recruitment to fetal-maternal interface, to increased IL-10 secretion, and to decreased local Th1/17 type cells that encourage anti-fetal cell activity; or
  natural killer cell (NK) of uterus or of peripheral blood, while the interacting leads to increased proliferation of cytokine-producing uterine NK cells or to reduced activation of peripheral blood cytotoxic NK cells (for example, such NK as CD16+ has an endogenous Fc(RIII-receptor specific to HCG, another NK as CD56+ has an endogenous adhesion molecule NCAM specific to HCG, both CD16+ and CD56+ might be of uterus or of peripheral blood), and, therefore, the interacting of NK with HCG leads to coordinated vascularization of placental bed and to reduced killing of fetal cells.

In some embodiments, the combination of cytokine and/or non-cytokine activators is selected complementary to a dynamics of expression or production of HCG by the patient's own PBMC in the culture media.

In some embodiments, the invention includes a kit for preventing or reducing the likelihood of implantation failure in a recipient of in vitro fertilization, the kit comprising a first device for preparation a portion of HCG, a second device for a culture media, a third device for measurements, a fourth device for injection, and optionally label marks, a portable computer, and a sensor for reading RFID (radio frequency identification). The device for measurements allows measuring of concentration of HCG in a culture media that contains HCG, PBMC and human recombinant albumin, all of which are diluted in a media suitable for culturing of PBMC, as, for example, a commercial media such as RPMI 1640.

In other embodiments, the invention relates to blood products having immuno modulation activity and increased endocrine signaling content, methods of manufacturing such blood products, compositions containing such blood products, and the applications of such blood products or compositions for female patients doing IVF, wherein these applications increase the chance of successful embryo implantation and pregnancy inception, compared to an IVF cycle without such applications In some embodiments, the invention includes a process of preparing a blood product applicable to a female patient undergoing an IVF treatment consisting steps as follows:

(a) In vivo preparing an organism of the patient to be ready for sampling of the patient's blood by means of modulating the patient's organism with at least one administration of at least one modulating agent, assuming that the latest (in time) administration is performed ΔT1 hours prior to taking of a blood sample from the patient (ΔT1 is from 30 to 40 hours; preferably 34 to 36 hours in advance of the blood sampling);

(b) Taking a sample of the patient's blood;

(c) Separating peripheral blood mononuclear cells (PBMC) from the blood sample (no later than 3 hours after the step (b));

(d) Putting the PBMC (obtained at previous step) into an introductory culture media (ICM);

(e) Culturing the PBMC in the ICM during a culturing time and achieving its transformation into a blood product at the end of the process's duration, e.g., approximately 20 to 80 hours after start of step (e) (preferably, 45+/−5 hours, more preferably, 48 hours after start of step (e)).

In some embodiments, the invention includes a blood product prepared according to the above process, wherein the preparation of the blood product is fully accomplished at the end of the process's duration. Such a blood product is referred to below as a first blood product.

In some embodiments, the introductory culture media (ICM) comprises components as follows:

(a) RPMI with L-glutamine and sodium bicarbonate, (b) human recombinant albumin, and (c) at least one supplementing agent or combination of supplementing agents.

In some embodiments, the invention includes a second blood product that is produced from the fully-prepared first blood product above, wherein production of the second blood product comprises steps as follows:

(a) taking a sample of the patient's blood at the time of the first product preparation process's finish, (b) separating fresh PBMC from the sample, (c) introducing these fresh PBMC into the first blood product, (d) briefly shaking these fresh PBMC in the first blood product and allowing them to mix with components of the first blood product (including the PBMC that have been in the culture media for the culturing time), and (e) extracting a resulting mixture of PBMC with modulating and supplementing agents from the culture, thereby obtaining the second blood product.

In some embodiments, in the production of this second blood product, prior to step (a), the patient organism is prepared for sampling of the patient's blood by means of an administration of a modulating agent, while the administration is performed ΔT2 hours prior to taking a blood sample from the patient (in a range 20-40 hours, preferably 24+/−2 hours).

In some embodiments, the modulating of step (a) is performed by such modulating agents as CRH, GnRH-A, HCG or other hormone assisting pregnancy or by combination of these hormones, so as to maintain a serum HCG level in a range of 150 to 350, preferably near 250 IU/mL in vivo in the patient at the time of sampling of blood (that can be achieved by intramuscular injection of 7,500 to 12,500 IU of HCG), or high cumulative presence of HCG+other hormone in blood.

In another embodiment, a composition containing H-hCG is administered to a patient during a period of time from a few days before implantation to a few days after it; while the administration aims to maintain the serum H-hCG at a level ranging from 0.1 to 10 nanograms per milliliter of serum during that period of time. For maintaining an effective concentration of H-hCG through an intravenous route of administration, an intravenous dose within the range 1 to 50 microgram at least once and up to four times a day can be applied.

In some embodiments, in the ICM, there is a supplementing agent such as CRH, HCG, LIF or other cytokine supporting embryo implantation or combination of these cytokines.

In some embodiments, during the culturing time at least one measurement of a concentration of HCG in the culture media is performed. In some embodiments, based on this measurement, at least one additional amount of HCG may be introduced into the culture media during the culturing time.

In some embodiments, some of the process steps may be performed in an IVF clinic, and others may be performed in a remote GMP facility. A destination time between steps performed in different places is preferably less than 2 hours.

In some embodiments, the invention includes a blood product having an immuno modulation activity and an increased endocrine signaling content due to presence of (a) peripheral blood mononuclear cells (PBMC) in amount of at least 4 million per milliliter, preferably at least 15 million per milliliter, even more preferably 50 million per milliliter, of the product; and (b) human chorionic gonadotropin (HCG) in amount of at least 150 international units (IU) per milliliter, preferably at least 500) IU per milliliter, of the product. In some embodiments, the HCG preferably is present in the blood product in an amount of 500 to 800 IU per milliliter, more preferably 600 to 700 IU/ml. The blood product may be in the form of a suspension having a viscosity allowing it to flow through a catheter medically-acceptable for an intrauterine injection to a female patient.

In some embodiments, the intrauterine injection is calibrated to deliver a dose of the suspension to the female patient undergoing IVF, wherein the dose for delivery has a volume in a range 0.10 to 0.35 milliliter, while the presence of PBMC is no less than 7.5 million cells per dose and may approach 25 million of mononuclear white blood cells per dose.

In some embodiments, about half to three-quarters of the PBMC in the suspension are the cultured PBMC that have been cultured in vitro in presence of HCG, while the rest of the PBMC are freshly extracted from the patient's blood.

In some embodiments, the cultured PBMC are produced in a sequence of steps as follows:

(a) Pre-activating a patient's blood in vivo by an intramuscular injection of HCG; preferably injecting HCG in amount about 10,000 (ten thousand) IU;

(b) Taking a sample of a patient's blood;

(c) Separating of PBMC from the sample taken on step (b);

(d) In vitro culturing of the PBMC, which have been separated on step (c), in a culture media having initial concentration of HCG about 400 to 800 IU per milliliter, preferably 550+/−50 IU/ml; while continuing this culturing for 40 to 80 hours, preferably 48+/−2 hours. At the end of step (d), a blood product containing the sufficiently cultured peripheral blood mononuclear cells is obtained.

In some embodiments, the intramuscular injection of HCG in step (a) is performed about 30 to 40 hours, preferably 33 to 37 hours, in advance of the step (b).

In some embodiments, the cultured PBMC are cultured at a manufacturing facility located no farther than a two-hour destination distance from a point of care (POC), such as an IVF clinic, whereas the ultimate production of the suspension, as a composition of cultured and fresh PBMC (e.g., the second blood product described above), is performed at the POC.

In some embodiments, the separating of PBMC from the blood sample (c) comprises:

preparing a test tube (1) containing about 5 ml of culture media (such as RPMI-1640), about 0.25 ml of a solution of protein HSA with its concentration of 10%, and about 1 ml of a solution containing about 5000 IU of human chorionic gonadotropin, and storing the test tube (1) in an incubator at a temperature of about 36.9-37.1° C. and a $CO_2$ concentration of about 5.7-6.2%;

preparing a test tube (2) containing approximately equal volumes of a buffered saline (such as media RPMI-1640) and blood taken from the patient in step (b), for example about 4.5 ml of RPMI-1640 and about 4.5 ml of blood;

preparing a test tube (3) containing about 4 ml of lymphocyte separation media (LSM), transferring about 6 ml of the diluted blood from test tube (2) into the test tube (3), on top of the LSM;

starting centrifugation of test tube (3) at radial velocity of about 1500 rpm;

preparing a test tube (4) containing about 5 ml of culture media (such as RPMI-1640), and storing it at a temperature of about 4 to 5° C. for about 40 minutes:

centrifuging test tube (3) at about 1500 rpm for about 40 minutes, to obtain heaviest (dark) fractions of a bottom layer, a PBMC layer (of lymphocytes and monocytes; having white color) above the bottom layer, and an upper layer (yellow) above the PBMC layer;

collecting PBMCs from the PBMC layer of test tube (3) (approximately 2 to 3 ml), and transferring them into test tube (4);

centrifuging test tube (4) for about 10 minutes at about 1600 rpm, to obtain a residue of collected PBMCs (the residue has a height of about ≤1 mm) at the bottom of test tube (4);

transferring the residue of collected PBMCs from test tube (4) into test tube (1), and placing test tube (1) in the incubator at a temperature of about 36.9-37.1° C. and a $CO_2$ concentration of about 5.7-6.2%; and optionally measuring a concentration of HCG in test tube (1), by taking a sample from test tube (1) approximately 1.5 hours after beginning the $CO_2$ incubation.

In some embodiments, the in vitro culturing of PBMC (d) comprises:

incubating test tube (1) above in the incubator at a temperature of about 36.9-37.1° C. and a $CO_2$ concentration of about 5.7-6.2%;

after about 24 hours of incubating test tube (1), gently shaking the test tube;

optionally measuring a concentration of HCG in test tube (1), at one or more time points during the culturing (e.g., at 24 hours and 48 hours) by centrifuging test tube (1) for about 10 minutes at 1600 rpm, then collecting a small liquid sample, such as about 0.25 ml from test tube (1), measuring the concentration of HCG in the sample using a dosimeter, and gently shaking test tube (1) and replacing it into the incubator for further culturing.

In some embodiments, after the in vitro culturing in step (d), a first blood product is obtained. In other embodiments, a second blood product then may be obtained, as follows:

taking a fresh sample of the patient's blood, and adding it to culture media (such as RPMI-1640) in a ratio of approximately one-to-one (e.g., about 4.5 ml of fresh blood and about 4.5 ml of RPMI-1640) in a test tube (5);

preparing a test tube (6) containing about 4 ml of lymphocyte separation media (LSM);

transferring about 6 ml of the diluted blood from test tube (5) into the test tube (6), on top of the LSM;

centrifuging test tube (6) at about 1500 rpm for about 40 minutes, to obtain separated dark fractions of a bottom layer, a PBMC layer above the bottom layer, and an upper layer above the PBMC layer;

preparing a test tube (7) containing about 5 ml of culture media (such as RPMI-1640), and storing it at a temperature of about 4 to 5° C. for about 40 minutes;

collecting the PBMCs from the PBMC layer of test tube (6) (approximately 2 to 3 ml), and transferring them into test tube (7);

centrifuging test tube (7) for about 10 minutes at about 1600 rpm;

transferring about 2 ml of freshly-separated PBMCs from test tube (7) into test tube (1);

centrifuging test tube (1) for about 10 minutes at about 1600 rpm, to obtain a residue of collected cultured and fresh PBMCs of height about 3 mm at the bottom of test tube (1);

optionally measuring a concentration of HCG in test tube (1), by taking a sample from test tube (1) after the above centrifuging; and transferring an amount (e.g., about 100 to 250 microliters, preferably 150 microliters) of the residue of collected cultured and fresh PBMCs from test tube (1) into a catheter, for performing intra-uterine injection of the PBMCs into the patient. In some embodiments, prior to being loaded with slurry of PBMC from the tube bottom's residue, the catheter has been pre-loaded with HCG.

In some embodiments, the invention relates to a method of reducing the likelihood of implantation failure during assisted reproduction in a female subject in need thereof comprising administering to the subject an effective amount of the above blood product (specifically, the second blood product), wherein at least part of the peripheral blood mononuclear cells are taken from the subject, and wherein an intrauterine injection of the product to the subject is applied prior to transfer of an embryo created in vitro.

In some embodiments, the injection is preferably applied 24 to 72 hours prior to embryo transfer.

In some embodiments, the use of the blood product allows treatment of such medical conditions as repeated implantation failure, high risk of autoimmune rejection of the transferred embryo, thin endometria, unreceptive endometria, age-related reduced fertility, high risk of age-related implantation failure, or unexplained infertility. In some embodiments, the use of the blood product improves a pregnancy rate for the subject in the IVF cycle, compared to infertility treatment without the blood product.

Accordingly, some embodiments relate to the use of the blood product (either the first blood product or the second blood product) in IVF treatment. Such embodiments relate to the blood product (either the first blood product or the second blood product) for use in IVF, wherein the use comprises introducing the blood product into the uterus of the female patient and transferring at least one embryo into the uterus of the female patient. Other embodiments relate to the blood product (either the first blood product or the second blood product), wherein the blood product is capable of decreasing an autoimmune reaction in a patient during the use of the blood product in the treatment of IVF.

Other embodiments relate to the blood product (either the first blood product or the second blood product) for use in the manufacture of a medicament for use in IVF treatment, in particular, for use in decreasing an autoimmune reaction in a patient during IVF treatment.

In some embodiments, the patient or subject is a mammal, for example murine, livestock, or human.

In some embodiments, the patient or subject is a human female of age ≥37 years old.

Some embodiments also relate to the use of the blood product (either the first blood product or the second blood product) for repairing, engineering, restoring, transplanting or treating tissue of a patient. Accordingly, some embodiments relate to the blood product (either the first blood product or the second blood product) for use in repairing, engineering, restoring, or treating tissue of a patient.

EXAMPLES

Infertile couples were admitted to clinical treatment. Among those admitted, the male factor of infertility was excluded. Some female patients had a history of RIF containing at least three unsuccessful IVF attempts including fresh- and cryo-IVF.

Oocytes were retrieved from the female patients using standard procedures known to those of ordinary skill in the art. Embryos were created using a variant of intracytoplasmic sperm injection (ICSI), and developmental kinetics were measured. Embryos were cryopreserved by vitrification.

Major steps, ingredients, conditions and duration of stages of the process of culturing, as well as procedures of administering the blood product are described in U.S. patent application Ser. No. 13/655,257, incorporated herein by reference.

As in U.S. patent application Ser. No. 13/655,257, the culture in the present examples contained 5 mL of commercially available media RPMI1640, 0.2 mL of commercially available human recombinant albumin, 1 mL of autologous PBMC and 1 mL of solution having 5000 IU of diluted HCG (obtained by dilution of commercially available dry powder of HCG), such that the total volume of culture was equal to 7.2 mL.

Differences between the procedures used in the present examples and those of U.S. patent application Ser. No. 13/655,257 were as follows.

In the examples in the present application, PBMCs were obtained from the blood of the patients (as in U.S. patent application Ser. No. 13/655,257). However, in the present examples, HCG was applied to the patients prior to obtaining the blood from which the PBMCs were obtained. In other words, the patients were pre-activated with HCG, prior to blood being taken from the patients for collection of PBMCs.

Additionally, in the examples in the present application, measurements were taken of the concentration of HCG, and, depending on the results of the measurements, changes in the procedure could be implemented in real time. In the present examples, for implementing changes in the culture, a device with a prepared solution of HCG was kept ready on standby.

Example 1 (Comparative)

A total of 180 female patients were treated, 90 according to the traditional ART protocol and 90 according to a modified protocol with the use of PBMC+HCG (as described in U.S. patent application Ser. No. 13/655,257; i.e., without intentionally targeted pre-activating the patients with HCG). All patients were of age 32 to 42 years, and had experienced three or more unsuccessful IVF attempts in the past. Two high quality embryos were transferred to every patient at every IVF attempt, fresh or cryo.

The results are summarized in the following Table 1, reproduced from U.S. patent application Ser. No. 13/655,257:

TABLE 1

|  | Group 1 (without PBMCs) | Group 2 (with PBMCs) |
| --- | --- | --- |
| Fresh-IVF | 22.2% (20 pregnancies after 90 ET) | 31.1% (28 pregnancies after 90 ET) |
| Cryo-IVF | 21.4% (15 pregnancies after 70 ET) | 41.9% (26 pregnancies after 62 ET) |
| Total | 38.9% (35 pregnancies for 90 patients) | 60.0% (54 pregnancies for 90 patients) |

As seen in Table 1, a combined PBMC+HCG therapy showed success in overcoming RIF, especially for patients undergoing cryo-IVF.

Example 2

Building on the success of Example 1, the inventors undertook a more comprehensive evaluation of the influence of HCG-dose, moment of time of the dose's administration, and other process parameters on the implantation success rate.

Eleven patients obtained a course of PBMC+HCG treatment similar to Example 1, prior to fresh embryo transfer (ET). Unlike in Example 1, however, the patients were intentionally pre-activated with HCG prior to blood being taken from the patients for collection of PBMCs. Four of the 11 patients had one or more poor quality embryos at the time of transferring, and no pregnancy was achieved among these four patients. For the remaining seven patients, embryos of high quality were transferred. Results for these seven patients are in the following Table 2:

TABLE 2

| 1 Pat. No. | 2 Age years | 3 Att. No. | 4 En mm | 5 $C_0$ | 6 $C_{24}$ | 7 $C_{48}$ | 8 Absolute increase $C_{48}-C_0$ | 9 Relative increase $C_{48}/C_0$ | 10 ? Dose of beta-hCG $0.2 \times C_{48}$ | 11 * Dose of total hCG IU | 12 Result |
| --- | --- | --- | --- | --- | --- | --- | --- | --- | --- | --- | --- |
| 1 | 33 | 2 | 11 | 4.8 | 5.2 | 9.6 | 4.8 | 2.0 | 1.92 | 300 | Pregnancy |
| 2 | 34 | 1 | 9 | 4.2 | 5.5 | 8.8 | 4.6 | 2.1 | 1.76 | 275 | Negative |
| 6 | 40 | 1 | 9 | 0.9 | — | 6.3 | 5.4 | 7.0 | 1.26 | 200 | Negative |
| 7 | 45 | 4 | 8 | 4.1 | 5.5 | 7.9 | 3.8 | 1.9 | 1.58 | 250 | Negative |
| 8 | 39 | 1 | 10 | 3.1 | — | 7.4 | 4.3 | 2.4 | 1.48 | 230 | Pregnancy |
| 9 | 34 | 5 | 9 | 5.9 | — | 10.1 | 4.2 | 1.7 | 2.02 | 315 | Pregnancy |
| 11 | 27 | 1 | 10 | 0.8 | — | 5.2 | 4.4 | 6.5 | 1.04 | 160 | Bio-chemic |

Table 2 includes measurements of the conditional concentration of beta-hCG in culture media, in IU/ml. In this context, "conditional" means that the measurement in culture media was performed by the test recommended for measuring beta-HCG in serum. Measurements were performed by beta-HCG ELISA assay (DRG Instruments GmbH, Germany). Numeration of patients (column 1) is in chronological order (patient No. 1 is the earliest one). In column 2, the patient's age is shown; in column 3, the number of IVF attempts; and in column 4, the thickness of endometrium prior to ET.

Measurements of the conditional concentration of beta-hCG were taken at different time points: $C_0$ was the initial concentration prior to the input of PBMC; $C_{24}$ was the concentration after 24 hours of culturing; and $C_{48}$ was the concentration after 48 hours of culturing, prior to adding a fresh portion of PBMC. The volume of each culture was: 5 ml RPMI media+0.2 mil albumin+1 ml HCG solution+1 ml PBMC=7.2 ml.

As seen in Table 2, the success rate (resulting pregnancies/treated patients) was 3/7 or 43%.

The average value of initial conditional beta-concentration (column 5, excluding patients 6 and 11) was $C_0$=4.42 IU/ml.

The average absolute increase of a conditional beta-concentration, in IU/ml, was 4.3 (column 8 of Table 2). The average relative increase (column 9, excluding patients 6 and 11) was 2.2 times.

Column 11 shows an estimate of the total dose of HCG delivered prior to ET. The estimated dose is calculated in accordance with the formula: Dose=$V \times K_{beta} \times C_{48}$, where V is a volume of delivered PBMC mixture equal to 0.2 ml, and $K_{beta}$ is an empirical coefficient establishing a correspondence between the measured conditional beta-HCG and the real total HCG.

$K_{beta}$ can be determined from the relationship between the average value of $C_0$ and total HCG as follows: $K_{beta} \times C_0$=5 000 IU/7.2 mi. Since the average value of $C_0$ was found to be 4.42 IU/ml, K. is 157. This value was used to estimate the total dose of HCG delivered prior to ET shown in column 11 of Table 2.

Of the seven patients in Table 2, successful implantation was achieved in three cases (1, 8, 9). In the other cases, (2, 6, 7, 11) the implantation was unsuccessful, including an unfortunate patient number 11, for whom a biochemical test showed a positive indication two weeks after ET, but three weeks after ET, the ultrasound test had not confirmed initiation of pregnancy.

Quantitative examination of data from Table 2 shows a correlation between HCG-parameters and the success rate of implantation.

Indicator Cutoff value of concentration of beta-HCG at moment of time T0: $C_0$=4.8 IU/ml. Two groups: $C_0^+ \geq 4.8$ for (1, 9), rate=2/2=100%; $C_0^- < 4.8$ for (2, 6, 7, 8, 11), rate=1/5=20%.

Indicator: Cutoff value of concentration of beta-HCG at moment of time T2: $C_{48}$=9.6 IU/ml. Two groups: $C_{48}^+ \geq 9.6$ for (1, 9), rate=2/2=100%; $C_{48}^- < 9.6$ for (2, 6, 7, 8, 11), rate=1/5=20%.

Indicator Cutoff value of dose of total HCG injected to the patient: Dose=300 IU. The same two groups as if considering the indicator $C_{48}$, because Dose=$V \times K$ beta$\times C_{48}$.

Example 3

Twenty-four patients obtained a course of PBMC+HCG treatment prior to fresh embryo transfer, similar to Example 2. Three of the 24 patients had poor quality embryos at the time for transferring, therefore it was decided to interrupt the procedure without performing ET on these three patients. For one other patient (out of the 24), a genetic analysis of an embryo suggested certain complications, and ET was not performed. For the remaining twenty patients, embryos of high quality were transferred. Results for these twenty patients are shown in Table 3 below:

TABLE 3

| Pat. No. | Age, years | Att. No. | Endometrium, mm | Day 0 $C_0$ | Day 1 $C_{24}$ | Day 2.1 $C_{47}$ | Day 2.2 $C_{49}$ | Dose IU | Result |
|---|---|---|---|---|---|---|---|---|---|
| 2 | 28 | 1 | 10 | 8.67 | 11.10 | 7.64 | 8.74 | 93 | N |
| 3 | 26 | 1 | 9 | 8.95 | 6.72 | 6.59 | 12.50 | 132 | N |
| 5 | 38 | 2 | 10 | 9.73 | 12.67 | 10.82 | 11.10 | 118 | pregnancy |
| 6 | 41 | 4 | 9 | 8.98 | 10.67 | 13.64 | 14.39 | 152 | N |
| 7 | 31 | 1 | 10 | 11.77 | 15.47 | 13.04 | 14.35 | 152 | N |
| 8 | 41 | 1 | 10 | 12.43> | 14.01 | 14.00 | 16.67> | 177 | N |
| 9 | 35 | 1 | 8 | 12.76> | 13.77 | 11.64 | 12.07 | 128 | pregnancy |
| 10 | 40 | 1 | 8 | 14.69> | 9.68 | 15.83 | 19.93> | 211 | pregnancy |
| 11 | 41 | 5 | 11 | 13.34> | 14.09 | 15.27 | 11.36 | 120 | pregnancy |
| 12 | 38 | 1 | 9 | 11.20 | 12.24 | 14.35 | 16.33> | 173 | pregnancy |
| 13 | 43 | 3 | 10 | 13.85> | 12.86 | 12.05 | 15.02 | 159 | N |
| 14 | 32 | 2 | 9 | 9.81 | 11.92 | 10.11 | 15.21 | 161 | N |
| 15 | 34 | 1 | 9 | 12.41> | 11.27 | 11.94 | 15.74> | 167 | pregnancy |
| 16 | 34 | 3 | 9 | 15.66 | 14.99 | 17.03 | — | ? | pregnancy |
| 17 | 40 | 1 | 9 | 19.87> | — | 15.51 | 13.79 | 146 | N |
| 18 | 35 | 1 | 8 | 13.32 | 18.52 | 19.59 | — | ? | N |
| 19 | 36 | 1 | 10 | 14.80> | — | 14.99 | 17.38> | 184 | N |
| 21 | 28 | 3 | 11 | 17.98> | — | 17.36 | 20.75> | 220 | pregnancy |
| 23 | 46 | 1 | 7 | 17.36 | 15.31 | 17.81 | — | ? | N |
| 24 | 29 | 4 | 13 | 14.33> | — | 16.33 | 12.65 | 134 | N |

Table 3 includes measurements of the conditional concentration of total HCG in culture media, in IU/mi. In this context, "conditional" means that the measurement in culture media was performed by the test recommended for measuring total HCG in serum. Measurements were performed by HCG ELISA assay (DRG Instruments GmbH, Germany). Numeration of patients (column 1) is in chronological order (patient No. 1 is the earliest one). In column 2, the patient's age is shown; in column 3, the number of IVF attempts (including six RIF patients); and in column 4, the thickness of endometrium prior to ET.

Measurements of the conditional concentration of total HCG were taken at different time points: $C_0$ was the initial concentration prior to the input of PBMC; $C_{24}$ was the concentration after 24 hours of culturing; $C_{47}$ was the concentration after 48 hours of culturing, prior to adding a fresh portion of PBMC, and $C_{49}$ was the concentration after 48 hours of culturing, immediately after adding a fresh portion of PBMC. The volume of each culture was: 5 ml RPMI media+0.2 ml albumin+1 ml HCG solution+1 ml PBMC=7.2 mi. The total dose was calculated in a manner similar to Example 2, but using the average initial value $C_0$=13.1 from Table 3. This resulted in an estimate for K of 53 from the relationship of K×$C_0$=5 000 IU/7.2 ml. The total dose then was calculated as 0.2×K×$C_{49}$.

As seen in Table 3, the success rate (resulting pregnancies/treated patients) was 8/20 or 40%.

Considering those patients who had two or more unsuccessful attempts prior to PBMC+HCG treatment, there were 6 RIF patients, and 3 became pregnant, for a rate of 3/6 or 50%.

Considering those patients for whom the present treatment was the second attempt of IVF, there were 2 patients, and 1 became pregnant, for a rate of 1/2 or 50%. This was the same as for the RIF patients above.

Considering those patients for whom the present treatment was the first attempt of IVF, there were 12 patients, and 4 became pregnant, for a rate of 4/12 or 33%.

Thus, the rate difference between first time treated IVF patients and others was 50/33=1.5 times. This shows that there is a certain difference in the rate of first-time treated patients and RIF patients.

Quantitative examination of data from Table 3 shows a correlation between HCG-parameters and the success rate of implantation. The patients (16, 18, 23) were excluded from further investigation, because there was no $C_0$ measurement accomplished.

Among 17 patients with all measurements, seven were positive. Rate=7/17=41%.

Indicator: $C_0$=12.4 IU/ml ($C_0^+$ corresponds to $C_0 \geq 12.4$ and $C_0^-$ corresponds to $C_0 < 12.4$). $C_0^+$=(8, 9, 10, 11, 13, 15, 17, 19, 21, 24)=>5/10=50%; $C_0^-$=(2, 3, 5, 6, 7, 12, 14)=>2/7=29%.

Rate difference with respect to this indicator=50/29=1.7 times

The following recommendation comes from these data: If $C_0$<12.4 then add some HCG to approach a positive indicator on Day 0.

Indicator: $C_{49}$=15.5 IU/ml ($C_{49}^+$ corresponds to $C_{49} \geq 15.5$ and $C_{49}^-$ corresponds to $C_4 < 15.5$). $C_{49}^+$=(8, 10, 12, 15, 19, 21)=>4/6=67%; $C_{49}^-$=(2, 3, 5, 6, 7, 9, 11, 13, 14, 17, 24)=>3/11=27%;

Rate difference with respect to this indicator=67/27=2.5 times

The following recommendation comes from these data: If $C_{47}$ or $C_{49}$<15.5, then add HCG or wait up to 24 hours additionally before performing ET.

Six patients had both indicators negative: $C_0^-$ and $C_{49}^-$=(2, 3, 5, 6, 7, 14). Only one of these six (patient number 5) became pregnant. Rate=1/6=17%. Conclusion: Two simultaneously negative indicators predict an implantation failure with probability of 83%.

Five patients had both indicators positive: $C_0^+$ and $C_{49}^+$=(8, 10, 15, 19, 21). Three of these five became pregnant. Rate=3/5=60%=>Approaching of such dynamics is desired. For patients 8 and 19, who had both indicators positive but who did not get pregnant, it appeared that an autoimmune situation might be operative, and further cryogenic protocol might be appropriate.

Example 4

Patient Number 9 of Table 2.

Patient 9 was a white married woman of age 34. Prior to admission to the PBMC+HCG treatment, she had four unsuccessful attempts of assisted reproductive technique (ART), one of which was fresh embryo transfer (ET) and three others were ET after cryo-preservation of embryos. None of these four attempts indicated even a bio-chemical pregnancy.

The fifth ART attempt was initiated with use of PBMC+HCG administration in March 2013. Both indicators $C_0$ and $C_{48}$ were achieved positively. Three embryos of high quality were transferred, the biochemical test showed a positive result two weeks after ET, and the ultrasound test confirmed a definitive pregnancy for one embryo three weeks after ET.

As of August 2013, a pregnancy of Patient 9 was ongoing under observation of fertility professionals.

Example 5

Patient Number 21 of Table 3)

Patient 21 was a white married woman. She had been a patient of the inventors' fertility clinic since 2011. As of 2011, there had been no pregnancy after over 2 years of marriage. Her husband's spermatogenesis, quantity and motility of spermatozoa, as well as genetic diagnostics, were without abnormalities. The factor of male infertility was almost excluded.

In 2011 the assisted reproduction technique in a form of artificial intrauterine insemination was applied, but did not lead to pregnancy.

In the beginning of 2012, an IVF cycle with "fresh" transfer of two embryos was performed; the thickness of endometrium was 13 mm as measured prior the transferring. One of these two embryos had linked to the endometrium, and clinical pregnancy was confirmed by the ultrasound test three weeks after ET. However, at the very early stage of this pregnancy, a spontaneous abortion happened (a few days after the ultrasound test).

In the second half of 2012, another IVF attempt with transfer of two thawed embryos after cryopreservation was performed; the thickness of endometrium was 12 mm then. This time there was no implantation success demonstrated (either by biochemical test or by ultrasound).

After the unsuccessful attempts above, the technology of PBMC+HCG was proposed to Patient 21 in 2013, and she was admitted to participate in a new IVF cycle. The recent Fresh-IVF procedure was performed in April 2013; Patient 21 was 28 years old then. After preliminary administration of PBMC+HCG, three high quality embryos were introduced into the uterine cavity having its endometrium of 11 mm. All three were successfully implanted as confirmed by ultrasound.

At the 7th week, the reduction of one embryo was executed. As of August 2013, the 17th week of pregnancy was proceeding with two remaining embryos and Patient 21 in good condition.

In all IVF attempts, only the embryos of high quality were transferred, and the thickness of endometrium was in the range from 11 to 13 mm. Thus, in case of Patient 21, not only the quality of embryo and thickness of endometrium were important, but also the mediating influence of the PBMC+HCG composition on the interaction of maternal body with semiallograft fetus was so helpful that resulted in a successful implantation and definitive pregnancy.

As it follows from the tables and examples above, the PBMC+HCG treatment according to embodiments of the invention delivers a similar or better success rate for RIF patients, compared with first-time IVF patients. This demonstrates the ability of the invention to overcome certain problems of RIF.

Without being bound by theory, the clinical results might be explained as follows. After culturing in HCG-enriched media, the PBMCs of a non-pregnant woman can themselves begin production of HCG and, therefore, the intrauterine delivery of such PBMCs prior to ET is capable of improving the endometrium preparation for ET, improving the maternal body's immunotolerance to ET, and overall increasing the probability of successful implantation of the embryo.

Differences between the doses that are shown in Tables 2 and 3 may be explained as follows. Estimations were performed with the use of empirical coefficients $K_{beta}$ (Table 2) and K (Table 3). The time of measurement (prior to or after adding fresh PBMC), the design of tests that are appropriate for measurements of HCG in serum, and the interaction of some components of the media with the test's reagents are possible reasons of observations reflecting such differences.

Additionally, there is a certain diversity in ELISA assays produced by dozen of manufacturers; some of assays can measure just one specific isoform of HCG; others can measure several isoforms; and some interfering is possible. The precision of measurements may be non-uniform for different isoforms measured by different assays. A discussion about metrological standard has been continuing for a long time. [Sturgeon et al 2009; Whittington et al & Grenache 2010; Cole 2013].

Despite these difficulties with empirical coefficients and diversity in ELISA assays, the inventors have demonstrated that a time-controlled treatment based on observed HCG dynamics both in culture media and in a patient's blood samples is effective for IVF.

Example 6

The above examples illustrate the improved success rate in treating IVF patients using embodiments of the present invention. In particular, the above examples show that RIF patients can benefit from such treatment. Although RIF can occur in younger patients, it tends to correlate with a patient's age. That is, among older females (age 38 years and over) who apply for IVF, a substantial portion of them suffer from RIF.

Based on the demonstrated ability of PBMCs to treat RIF, and the known fact that many older patients suffer from RIF, the inventors hypothesized that the age-related risk of implantation failure may overlap, in etiology, with the risk of RIF. Accordingly, in the following example, the inventors analyzed the usefulness of PBMC treatment for all patients over 38 years of age, independently of the number of previous IVF attempts.

In a clinical trial, a PBMC treatment was offered (at a subsidized price) to all IVF female patients of age ≥38 to ≤45 years with BMI of 18 to 32 kg/m2 and a normal uterine cavity without uterine disease (visible on pelvic ultrasonography), who had at least two top quality embryos (own, non-donated) for the transfer. Exclusion criteria were: any serious systemic disease or endocrine disorders (e.g., diabetes mellitus or untreated thyroid dysfunction); uterine myoma or previous myomectomy; presence of hydrosalpinges; also endometriosis in the severe form.

Patients who agreed to take the PBMC treatment formed a treatment group (N=94) and proceeded to the study under IRB approval; those who declined were the control (N=39). The subgroups were: 49 patients of age 38-40 in PBMC group vs 24 in control; 26 patients of age 41-42 in PBMC group vs 12 in control; also 19 patients of age 43-45 in PBMC group vs 3 in control; as shown in Table 4 below.

Embryo transfer (ET) of two top quality embryos was performed 24 to 72 hours following PBMC injection. After such ET, clinical pregnancy was determined by means of standard ultrasound diagnostics. Chi-squared test was used for statistical analysis of differences between the patient groups.

Prior to taking the patient's blood samples for separation of PBMC, an intramuscular injection of HCG was administered in a certain amount per dose.

A first amount of HCG was administered prior to obtaining a first portion of fresh blood from a patient, and a second amount of HCG was administered prior to obtaining a second portion of fresh blood from the same patient. The first portion of the patient's blood was used to prepare a first blood product according to an embodiment of the invention, while both the first and second portions of the patient's blood were used to produce a second blood product according to an embodiment of the invention.

Second blood products of autologous PBMC with human chorionic gonadotropin (HCG) were produced and applied prior to embryo transfer (ET) in fresh- and cryo-IVF protocols similar to those described in U.S. application Ser. No. 13/655,257. However, the present example did not categorize fresh vs cryo cases. The composition was delivered through a catheter as an intrauterine injection in an amount of 0.15 mL of a suspension containing PBMC cells and HCG. The results are shown in Table 4 below.

TABLE 4

| Group | Age 38-40 | Age 41-42 | Age 43-45 | Total | Pregnant | Pregnancy Rate |
|---|---|---|---|---|---|---|
| PBMC (Preg) | 49 (30.6%) | 26 (23.1%) | 19 (21.1%) | 94 | 25 | 25/94 = 26.6% |
| Control (Preg) | 24 (25.0%) | 12 (16.7%) | 3 (0.0%) | 39 | 8 | 8/39 = 20.5% |

As seen in Table 4, the clinical pregnancy rate in the PBMC group (26.6%) was 30% higher than in the control group (20.5%). 25/94 patients became pregnant in the PBMC group vs 8/39 patients in the control (p=0.46).

These observations were rather favorable for the use of PBMC, especially since the oldest subgroup of 43-45 years of age was disproportionally larger in the PBMC group, than in the control group (19/94 vs 3/39). Among the oldest patients, there were 4/19 pregnancies with PBMC use and 0/3 without it (p=0.38).

The pregnancy rate (PR) decreased with age in both the PBMC and control groups of patients. However, among the PBMC-treated patients, the PR decreased less sharply compared to the control group.

These results demonstrate a tendency of steady increasing of the gap between the PR of PBMC-treated patients and the PR of control patients with increasing patient age. These PR were 30.6% vs 25.0% for ages 38-40, 23.1% vs 16.7% for ages 41-42 and 21.3% vs 0% for the oldest subgroup of ages 43-45 in the trial. Thus, when stratified by age, subgroups of older patients had a larger gap between the success rate in treated and control patients compared to the gap for younger patients.

These results suggest a benefit of intrauterine use of PBMC+HCG for females over 38, and this is a promising improvement compared to traditional IVF. Without being bound by theory, the inventors hypothesize that the reproductive system of older female patients requires a longer time to prepare for acceptance of the arriving embryo in IVF treatment. The use of PBMC+HCG prior to ET leads to 1) early signaling of immune cells to the mother's body to be prepared on the systemic level, and 2) early preparation of endometrium environment on the local level. These two mechanisms may provide effective overcoming of age-related unpreparedness for ET and, therefore, result in better inducing of pregnancy in case of PBMC-enhanced IVF treatment, compared to conventional one.

It is natural to expect that an older organism works slower in immune/endocrine aspects. However, if a clinician initiates preparation for embryo acceptance in advance of its arriving, even a slow-working organism can be ready at the proper time. Again without being bound by theory, the injection of PBMC+HCG might mimic the presence of an embryo inside the patient even before the embryo is present. In this way, the preparation for embryo acceptance begins in advance; hence, when the embryo actually arrives, the organism is already tuned to attach it to the endometrium. Such an understanding is built on the facts that: 1) HCG is the first cytokine that embryo is producing for earliest signaling to mother's organism about its presence; 2) HCG is an active participant of fetal-maternal cross talk important to implantation; 3) embryo presence induces the endometrium for local secretion of HCG in return; 4) HCG mediates a cascade of the organism's processes that are important to pregnancy inception, maintaining and development; particularly, HCG modulates several endometrial parameters as endometrial differentiation (IGFBP-1), angiogenesis (VEGF), implantation (LIF, M-CSF) and tissue remodeling (MMP-9); 5) HCG can be bound with certain cells of PBMC variety, be released by such cells, and be transported by means of PBMC throughout the organism; 6) rapid increase of HCG concentration in female's fluids is an important attribute of healthy pregnancy inception; and finally 7) bio-chemical pregnancy test is based on the measurement of HCG, exactly.

This example shows that the age-related risk of implantation failure can be significantly reduced by using embodiments of the present invention, compared to using traditional IVF.

The invention claimed is:

1. A method for preparing a composition comprising:
    isolating a first portion of isolated peripheral blood mononuclear cells (PBMCs from the blood of a female patient, and
    culturing the PBMCs in vitro in the presence of at least 500 IU/ml of hCG;
    further comprising administering hCG at a time T0 to the female patient in an amount sufficient to maintain a serum hCG level of 250 IU/ml until the first portion of PBMCs is isolated at a time T1;
    wherein said composition comprises the first portion of PBMCs at a concentration of at least $15 \times 10^6$ cells per milliliter that have been obtained from a female patient at time T1, and human chorionic gonadotropin (hCG) at a concentration of at least 500 international units (IU) per milliliter.

2. The method of claim 1, wherein the female patient is intramuscularly administered hCG at time T0 in an amount sufficient to maintain serum hCG at 250 IU/ml until time T1 and wherein the time T1 is 30 to 40 hours after the time T0.

3. The method of claim 1, further comprising culturing the first portion of isolated PBMCs in vitro in a medium containing a concentration of at least 500 international units/ml of hCG from a time T1 until a time T2, wherein T2−T1 ranges from 20 to 80 hours.

4. The method of claim 3, further comprising measuring a concentration of hCG in the PBMC culture at least once during the period from T1 to T2, and, optionally introducing at least one additional amount of hCG into the culture during this period.

5. The method of claim 1, further comprising isolating a second fresh portion of PBMCs from the female patient at a time T2 after the collection of the first portion of PBMCs at time T1, wherein T2−T1 ranges from 20 to 80 hours;
    combining the isolated second fresh portion of PBMCs with the cultured PBMCs from the first portion in a medium containing at least 500 IU/ml of hCG; and
    resuspending the combined first and second portions of PBMCs at a concentration of at least $15 \times 10^6$ PBMCs/ml.

* * * * *